United States Patent [19]

Cartmell et al.

[11] Patent Number: 5,447,492

[45] Date of Patent: Sep. 5, 1995

[54] EXTERNAL FIXATION DRESSING FOR ACCOMMODATING A RETAINING PIN

[75] Inventors: James V. Cartmell, Xenia; Michael L. Wolf, West Milton; Wayne R. Sturtevant, Centerville, all of Ohio

[73] Assignee: New Dimensions in Medicine, Inc., Dayton, Ohio

[21] Appl. No.: 169,372

[22] Filed: Dec. 20, 1993

[51] Int. Cl.⁶ ............................................. A61F 13/00
[52] U.S. Cl. ....................................... 602/58; 602/41; 602/48; 602/59; 606/53; 606/54; 606/59; 604/180
[58] Field of Search ............... 602/41, 42, 48, 58, 602/59; 606/54, 59, 151, 53; 128/853, 854, 888; 604/180

[56] References Cited

U.S. PATENT DOCUMENTS

| | | | |
|---|---|---|---|
| 3,683,911 | 8/1972 | McCormick | 604/180 |
| 4,856,504 | 8/1989 | Yamamoto et al. | 604/180 |
| 4,941,882 | 7/1990 | Ward et al. | 604/180 |
| 4,988,341 | 1/1991 | Columbus et al. | 128/888 |
| 5,059,424 | 10/1991 | Cartmell et al. | 424/443 |
| 5,080,661 | 1/1992 | Lavender et al. | 606/54 |
| 5,115,801 | 5/1992 | Cartmell et al. | 602/57 |
| 5,160,328 | 11/1992 | Cartmell et al. | 602/41 |
| 5,207,652 | 5/1993 | Kay | 604/180 |
| 5,266,401 | 11/1993 | Tollini | 604/180 |

*Primary Examiner*—Paul Prebilic
*Attorney, Agent, or Firm*—Killworth, Gottman, Hagan & Schaeff

[57] ABSTRACT

A flexible external fixation dressing product contains a clear hydrogel material in a gel-like phase. The fixation dressing product is comprised of several layers including a thin-film top layer, optional backing layer, optional support layer, hydrogel layer, and optional release liner, and is adapted for use around the retaining pins of an external fixation device. The thin-film top layer may define a center portion and a perimeter portion. The backing layer, support layer and hydrogel material are positioned in the center portion of the thin-film top layer. The porous backing layer is formed of a porous material having sufficient porosity that the backing layer can be secured to the hydrogel material without the use of an adhesive. During manufacture, the dressing product is assembled and a substantially centered opening and a slit are cut. The opening and slit extend through all layers of the dressing and may also extend through the release liner, if included. The slit extends from an outer edge of the dressing and intersects the opening.

30 Claims, 4 Drawing Sheets

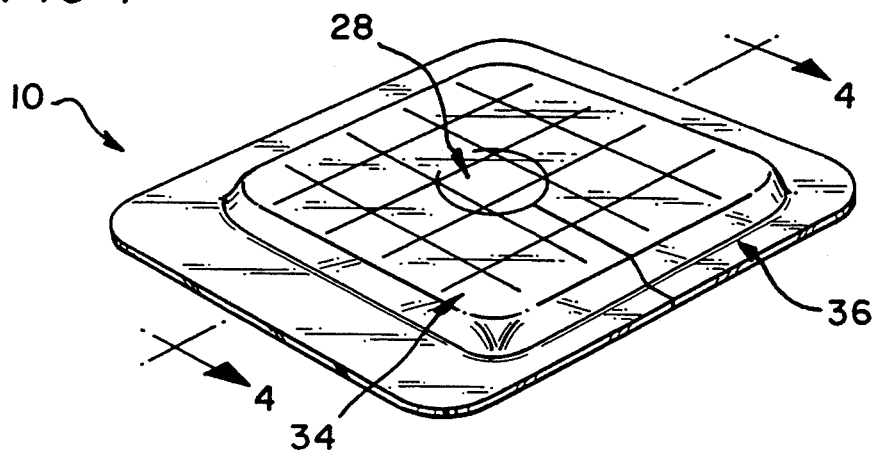
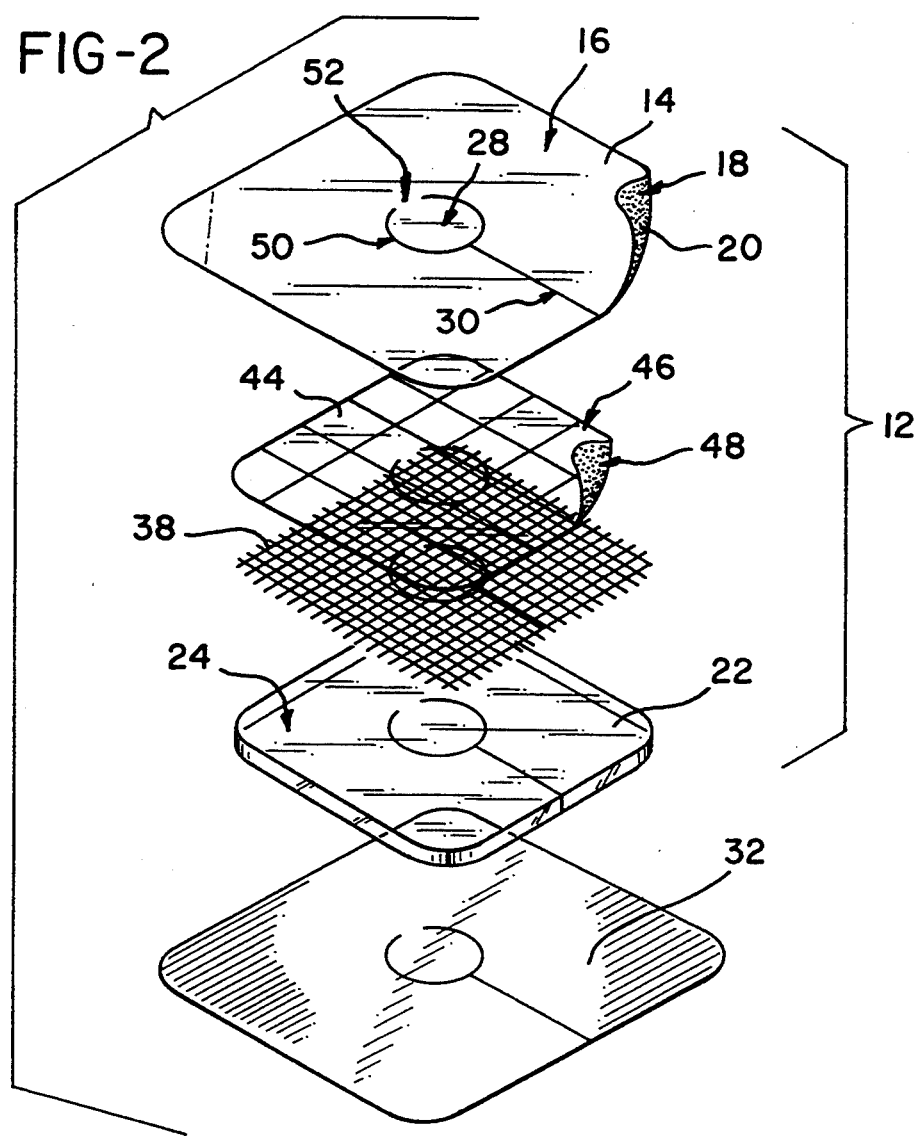

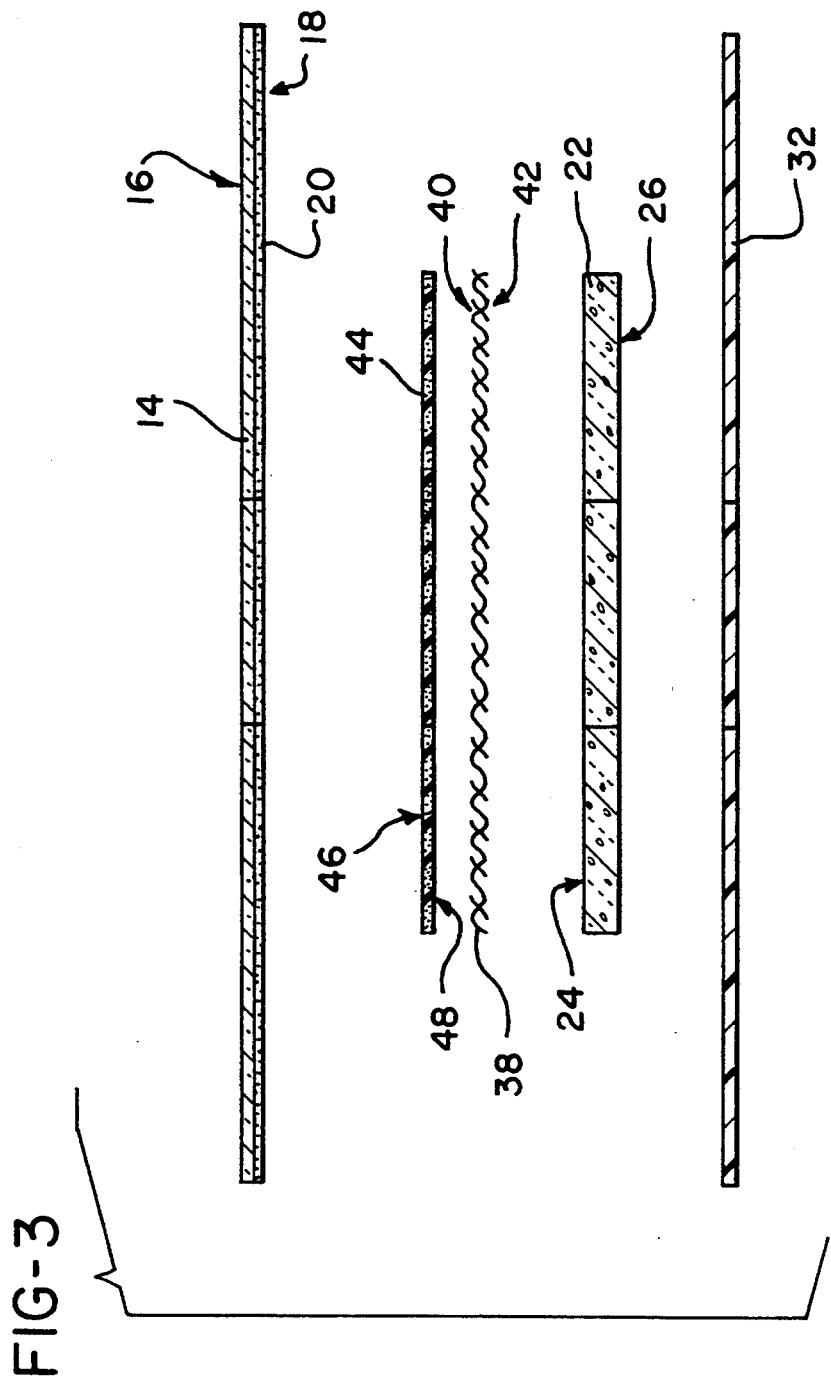

EXTERNAL FIXATION DRESSING FOR ACCOMMODATING A RETAINING PIN

BACKGROUND OF THE INVENTION

The present invention relates to wound dressings and, more particularly, to an external fixation dressing product containing a hydrogel substance and an opening which accommodates a retaining pin.

External fixation devices are widely used by medical personnel when treating patients with severely broken limbs. Holes are drilled into several places along the broken bone, and retaining pins are placed in the holes. The pins extend outward in a generally perpendicular direction from the broken bone. A series of connected rods having appropriately-spaced holes therewithin is mounted over the pins. Such a device secures the fracture in place after it has been properly set, thereby allowing the bone to heal.

It has been discovered that infection frequently results from the use of external fixation devices. If left uncovered, the areas immediately surrounding the holes in the patient's skin through which the pins extend are susceptible to bacteria and crusted organisms. Further, many prior art bandages used to cover the areas surrounding the retaining pins consist of a gauze material. Being opaque, such a material does not permit medical personnel to monitor the healing of the wound easily. Further, a gauze material may form an actual adhesive attachment that would damage new cell tissue upon removal.

It is often desirable to allow a wound to heal in a slightly moist or occlusive state, as it is believed that this may accelerate healing. It is important, therefore, that excess wound exudate be removed. If excess wound exudate remains on a wound, a "blister" of exudate can form under the wound dressing, which is not only unsightly, but also may cause the dressing to leak, thereby defeating the aim of sterility. Additionally, it is not desirable to remove all exudate, as that would result in a dry wound and, hence, a slower healing process. Existing methods of aspiration, however, can lead to infection or destroy sterility.

Many dressings currently adapted for use around retaining pins do not maintain a tight seal between the dressing and the retaining pin. These prior art dressings, therefore, do little to prevent bacteria and other organisms from coming into contact with the wound. Further, the method of manufacturing some prior art dressings involves die-cutting holes in the dressing in order to accommodate the retaining pins. The portion of the dressing that is cut out must be disposed of and, often, causes the die to clog.

It is seen, therefore, that there is a need for a moist hydrogel wound dressing product for use with an external fixation device. Further, there is a need for transparent external fixation dressing that allows medical personnel to monitor the healing of the wound, for an external fixation dressing that forms a relatively tight seal around a retaining pin in order to minimize the risk of infection of the wound, and for a method of manufacture that eliminates disposable portions of external fixation dressings.

SUMMARY OF THE INVENTION

The present invention meets these needs by providing a thin-film external fixation dressing containing a hydrogel material. The present invention also provides a method of manufacture of the external fixation dressing. The external fixation dressing product herein can be manufactured to any desired size to provide a thin-film, fluid-absorbing dressing that fits around a retaining pin of any size. The external fixation dressing herein is conformable, adhesive to the patient's skin surrounding the retaining pin, and contains an opening properly sized to accommodate a retaining pin such that a relatively tight seal is maintained between the retaining pin and the dressing. In accordance with one aspect of the present invention, an external fixation dressing for bandaging the area around an external fixation retaining pin comprises a thin-film top layer, a first adhesive layer, a backing layer, a hydrogel layer, and a support layer. The hydrogel layer has a first side and a second side and is comprised of a clear, aqueous, polyurethane, hydrogel material. The support layer has a first side and a second side and comprises a permeable fabric having a plurality of interstices therewithin. The support layer is disposed on the first side of the hydrogel layer. The hydrogel material, which is in liquid form prior to curing, penetrates the interstices within the support layer, thereby resulting in the presence of the hydrogel layer on both the first and second sides of the support layer.

The thin-film top layer has a first side and a second side and defines a center portion and a perimeter portion which surrounds the center portion. The first adhesive layer is positioned on the second side of the top layer. The second side of the top layer is attached to the first side of the hydrogel layer by means of the first adhesive layer, such that the first side of the support layer is adjacent to the second side of the top layer. The support layer, hydrogel layer, and top layer are appropriately sized in order that the support layer and hydrogel layer reside entirely within the center portion of the second side of the top layer.

The dressing also includes a backing layer with a first side and a second side. In one embodiment, a backing layer comprising polyurethane is utilized, and a second adhesive layer is positioned on the second side of the backing layer. The second side of the polyurethane backing layer is adhered to the first side of the hydrogel layer by means of the second adhesive layer, such that the first side of the support layer is adjacent to the second side of the backing layer. Alternatively, a backing layer comprising a porous material may be used, thereby allowing the second side of the backing layer to be adhered to the first side of the hydrogel layer without the use of a second adhesive layer. Preferably, the porous backing layer is formed of a filled polyolefin foam. The first side of the backing layer is adhered to the center portion of the second side of the top layer by means of the first adhesive layer. If a transparent backing layer is used, the backing layer may further contain a printed grid in order to allow medical personnel to monitor the healing of the wound beneath the dressing. The grid may be in any shape, but is preferably rectangular in shape. The grid may also be printed on the transparent, thin-film top layer.

The dressing defines a substantially centered opening that extends through the top layer, first adhesive layer, backing layer, hydrogel layer, and support layer. If a second adhesive layer is incorporated, the opening extends through this layer, as well. The opening is sized to receive a retaining pin such that a relatively tight seal is maintained between the bandage and the retaining pin. The opening may be defined by a C-shaped cut and a hinged portion, or, alternatively, by an asterisk-shaped plurality of intersecting cuts.

The dressing may further define a slit which extends from an outer edge of the dressing and intersects the opening. The slit extends through the top layer, first adhesive layer, backing layer, hydrogel layer and support layer. The slit also extends through the second adhesive layer if this layer is included.

The dressing may also comprise an optional release liner. In embodiments in which the top layer defines a perimeter portion and a center portion, the release liner completely overlies the hydrogel layer and is secured to the perimeter portion of the second side of the top layer by means of the first adhesive layer.

The present invention also provides a method of manufacturing the external fixation dressing product. Initially, the thin film is provided, preferably of a polyurethane material. This film contains a first side and an opposing second side. The second side of the thin film is coated with a preferably medical-grade adhesive layer. A hydrogel material is then applied to the second side of the thin-film top layer.

The method of manufacture of the present invention further comprises the step of cutting a slit and a substantially centered opening in the dressing. In a preferred embodiment, the slit extends from an outer edge of the dressing and intersects the opening, and the slit and opening extend through the top layer, adhesive layer, and hydrogel material. If an optional support layer or backing layer is utilized, the slit and opening also extend through these layers. The opening is appropriately sized to receive a retaining pin and to maintain a relatively tight seal between the retaining pin and the dressing.

In one embodiment, the opening may consist of a C-shaped cut in the dressing. As should be apparent, a C-shaped cut will produce a hinged portion, as well. When the dressing is fitted over a retaining pin, the cut portion will be displaced away from the patient's skin, but will remain attached to the remainder of the dressing by means of the hinged portion. Alternatively, an opening may be cut which consists of an asterisk-shaped plurality of intersecting cuts.

It is an object of the present invention to provide an external fixation dressing containing a moist hydrogel material, which facilitates healing and may be removed without damaging new cell tissue around the wound; to provide a transparent external fixation dressing that allows medical personnel to monitor the healing of the wound; to provide an external fixation dressing that forms a relatively tight seal around a retaining pin in order that the risk of infection may be minimized; and to provide a method of manufacturing an external fixation dressing, whereby no parts of the dressing are discarded.

BRIEF DESCRIPTION OF THE DRAWINGS

FIG. 1 is a perspective view of one embodiment of the external fixation dressing of the present invention.

FIG. 2 is an exploded perspective view, illustrating the layers which form a preferred embodiment of the external fixation dressing product.

FIG. 3 is an exploded side view of the external fixation dressing product of FIG. 2.

DETAILED DESCRIPTION OF THE PREFERRED EMBODIMENTS

Figure 4:
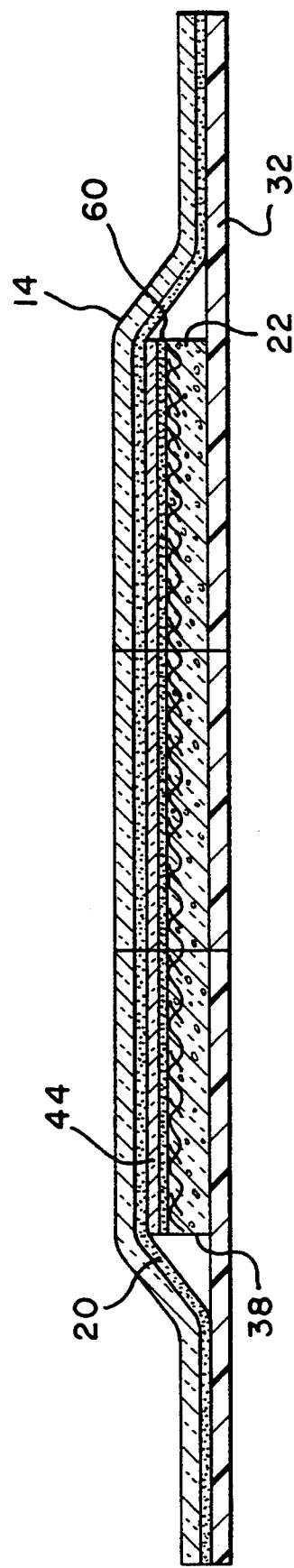
FIG. 4 is a cross-sectional view of a second embodiment of the external fixation dressing product of the present invention.

The present invention relates to an external fixation dressing product for use with an external fixation device and its associated retaining pins. The invention also includes a method of manufacturing the external fixation dressing product.

Referring to FIGS. 1–3, the external fixation dressing product 10 of the present invention is shown. Although the external fixation dressing product 10 is illustrated in FIG. 1 as having a rectangular shape, it may be configured in any of a variety of desired shapes. The external fixation dressing product 10 is composed of an external fixation dressing 12 and a release liner 32. The external fixation dressing 12 includes a thin-film top layer 14, preferably of polyurethane, which has a first side 16 and a second side 18, the second side 18 being coated with an adhesive layer 20. When the dressing 12 is applied, the first side 16 of the top layer 14 forms the outer surface of the dressing 12. The top layer 14 may, alternatively, be constructed of materials other than polyurethane, such as polyethylene, vinyl, or other suitable materials, and may also be perforated throughout in order to improve the moisture- and vapor-permeability of the dressing 12.

The dressing 12 further comprises a hydrogel layer 22 which has a first side 24 and a second side 26. The hydrogel layer 22 is positioned on the second side 18 of top layer 14 such that the adhesive layer 20 resides between the hydrogel layer 22 and the second side 18 of top layer 14. The dressing product 12 defines a substantially centered opening 28 which extends through top layer 14, adhesive layer 20, and hydrogel layer 22. The opening 218 may also extend through the release liner 32, although this is not required.

Figure 6:
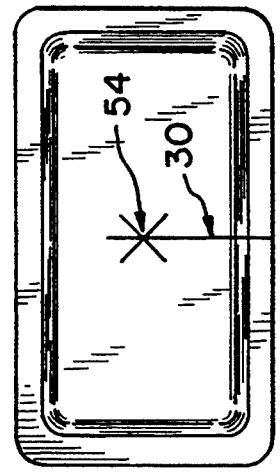
FIG. 6 is a top view of the external fixation dressing, illustrating an opening formed by intersecting cuts.

In one preferred embodiment of the present invention, shown in FIGS. 1–3 and FIG. 5, as well, the opening 28 is defined by a C-shaped cut 50 and a hinged portion 52. Alternatively, the opening 28 may be defined by an asterisk-shaped plurality of intersecting cuts 54, as illustrated in FIG. 6. A principal advantage of the C-shaped cut 50 and hinged portion 52, and the asterisk-shaped cuts 54, is that no waste is produced when these openings 28 are cut, and no portion of the dressing is discarded. If a complete hole were to be punched or die cut through the dressing, the portion of the dressing removed to make the hole would present handling and disposal problems. A series of such dressing portions would be produced, tending to clog equipment and requiring special handling. Since no such waste portions are produced with the present invention, these problems are obviated.

The preferred hydrogel material for use in hydrogel layer 22 is formed from an aqueous mixture including from about 0% to about 90% by weight polyhydric alcohol; from about 6% to about 60% by weight aliphatic diisocyanate-terminated prepolymer; from about 4% to about 40% by weight polyethylene oxide-based polyamine; up to about 2% by weight sodium chloride; and the balance water. A more preferred hydrogel composition for forming hydrogel layer 22 comprises from about 15% to about 30% by weight of a polyhydric alcohol selected from a group consisting of polypropylene glycol, polyethylene glycol and glycerine, from about 8% to about 14% by weight isophoronediisocyanate-terminated prepolymer, from about 5% to about 10% by weight polyethylene oxide-based diamine, up to about 1% by weight of a salt, and the remaining percentage water. Most preferably, hydrogel layer 22 includes 17% polypropylene glycol, 12% isophoronediisocyanate-terminated prepolymer, 9% polyethylene oxide-based diamine, 1% salt, and 61% water. The hydrogel layer 22 provides a biocompatible, nonirritating, fluid-absorbing, bacterial-protective, cushioning, skin-like media over the wound site.

In a preferred embodiment of the present invention, the top layer 14, adhesive layer 20, and hydrogel layer 22 are transparent, thus enabling medical personnel to monitor the healing and cleanliness of the patient's skin.

Figure 7:
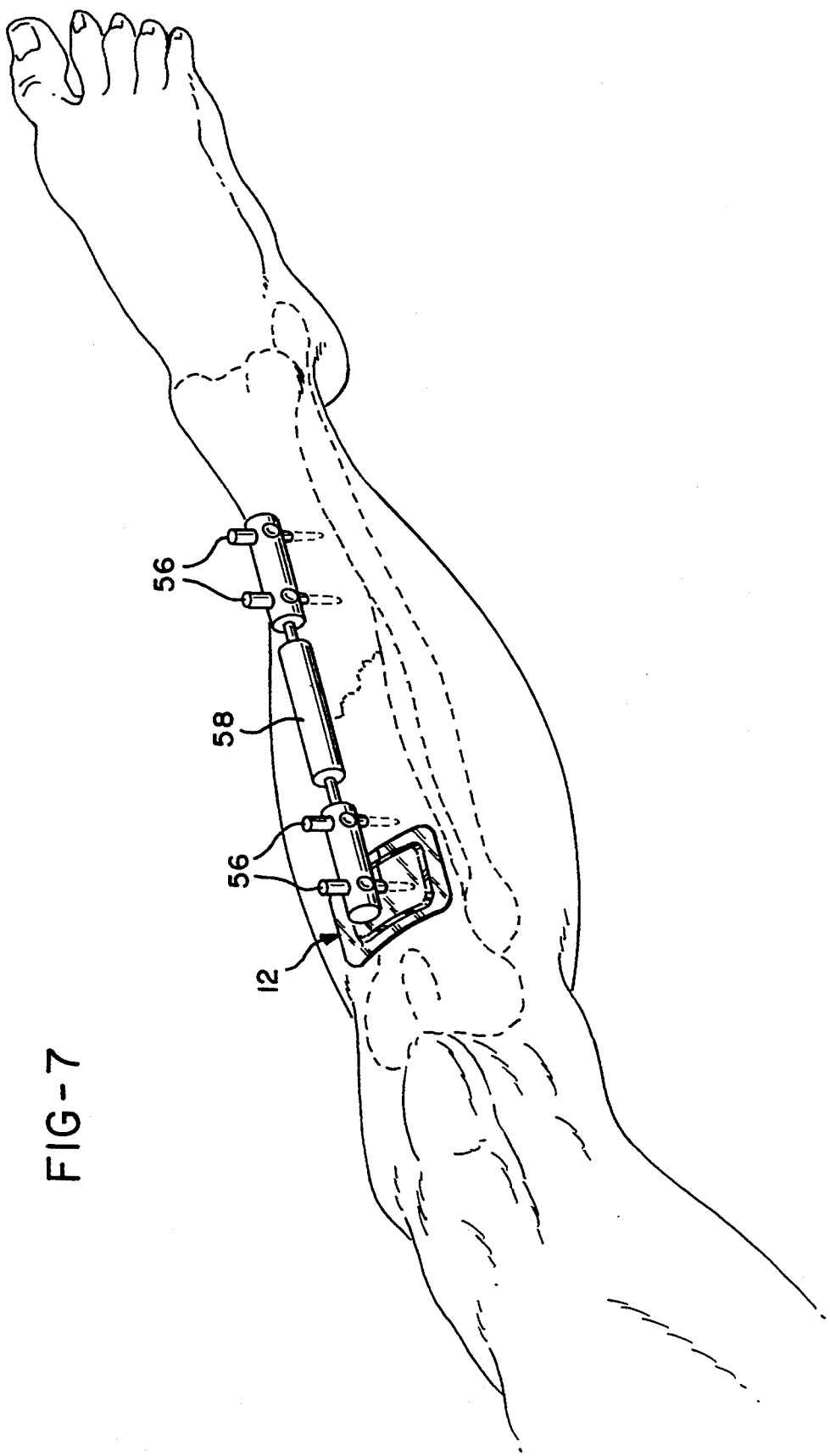
FIG. 7 is a perspective view showing an external fixation dressing in place on the patient's skin and around a retaining pin.

The external fixation dressing 12 may further define a slit 30 which extends from an outer edge of the dressing product 10 and intersects opening 28. The slit 30 extends through the top layer 14, adhesive layer 20, and hydrogel layer 22. The slit allows medical personnel to slip the dressing 12 around a retaining pin 56 (FIG. 7) of an external fixation device 58 without disturbing or removing the device 58. Although FIG. 7 shows only one dressing 12 in place, a dressing 12 is preferably utilized around wounds at the site of each retaining pin 56.

In the illustrated embodiment of the present invention, the top layer 14 defines a center portion 34 and a perimeter portion 36. The hydrogel layer 22 resides entirely within the center portion 34 on the second side 18 of top layer 14, and the optional release liner 32 is secured to the perimeter portion 36 of the second side 18 of top layer 14 by means of adhesive layer 20. After the optional release liner 32 is removed prior to application of the dressing 12, the adhesive layer 20 on the second side 18 of top layer 14 serves to adhere the dressing 12 to the patient's skin.

The dressing 12 may optionally also include a support layer 38. The support layer 38 is composed of a permeable fabric with a plurality of interstices therewithin, and is, preferably, made from a material such as a woven or nonwoven fabric, gauze, scrim, or other similar material. The support layer 38 has a first side 40 and a second side 42, with the second side 42 being secured to the first side 24 of hydrogel layer 22. The hydrogel layer 22 preferably penetrates the interstices of the support layer 38 to the first side 40 of the support layer 38, such that the hydrogel layer 22 actually resides on both the first side 40 and the second side 42 of support layer 38. As a result, hydrogel layer 22 is adhered to the second side 18 of top layer 14 by means of adhesive layer 20, such that the first side 40 of support layer 38 is adjacent to the second side 18 of top layer 14.

The dressing 12 may optionally also include a backing layer 44, having a first side 46 and a second side 48. Backing layer 44 is positioned between the hydrogel layer 22 and the second side 18 of top layer 14. The backing layer 44 is adhered to the second side 18 of top layer 14 by means of adhesive layer 20. The backing layer 44 is, preferably, constructed of a porous material having sufficient porosity such that the second side 48 of backing layer 44 is secured to the first side 24 of hydrogel layer 22 without the use of a separate adhesive layer. The porous material preferably comprises a filled polyolefin foam, wherein the porous material has a porosity ranging from about 30% to about 80%. The preferred porous material is a microporous synthetic sheet commercially available from PPG Industries, Inc., under the trademark Teslin ®. Those skilled in the art will understand the extent to which the porous material must be porous will depend upon the particular gel material chosen to form the hydrogel layer 22. Further, those skilled in the art will appreciate that sufficiently porous materials other than those described herein may be used without departing from the scope of the invention.

In addition to the porous material discussed above, backing layer 44 may alternatively comprise a transparent polyurethane film, as depicted in the cross-sectional view of a second embodiment of the fixation product 10 shown in FIG. 4. In this embodiment, a second adhesive layer 60 may be included. Second adhesive layer 60 is positioned on the second side 48 of backing layer 44 and provides a means for adhesively attaching the second side 48 of backing layer 44 to the first side 24 of hydrogel layer 22.

In embodiments incorporating the optional support layer 38 and the optional backing layer 44, opening 28 and slit 30 extend through support layer 38 and backing layer 44. The opening 28 and slit 30 may, but need not, extend through optional release liner 32.

The present invention further includes a method of manufacturing an external fixation dressing product 10. Initially, the second side 18 of the thin-film top layer 14 is coated with a medical-grade adhesive layer 20. Hydrogel material 22 is then applied to the second side 18 of the thin-film top layer 14, and cured in place.

When the optional support layer 38 is to be included, the hydrogel material 22 is applied to the second side 42 of the support layer 38. The interstices within the fabric of the support layer 38 allow the hydrogel material 22 to flow through to the first side 40 of support layer 38, such that the hydrogel material 22 resides on both the first side 40 and the second side 42 of support layer 38. The first side 40 of support layer 38, along with hydrogel material 22, is secured to the second side 18 of top layer 14, and the hydrogel is cured in place.

If the optional support layer 38 is not included, the hydrogel material 22 is applied directly to the adhesive layer 20 on the second side 18 of top layer 14, and cured in place. An optional release liner 32, preferably of a silicone-coated sheet material, may then be laminated to the hydrogel material 22, and the adhesive 20 on the periphery of top layer 14.

If the backing layer 44 is to be included in the dressing 12, it is secured to the top layer 14 and then the hydrogel material 22, with or without the support layer 38, is positioned over the backing layer 44. The hydrogel material is then cured in place.

The method of manufacture further may comprise the step of cutting a slit 30 and a substantially centered opening 28 in the dressing product 10. In one embodiment, the slit 30 extends from an outer edge of the dressing product 10 and intersects the opening 28. The slit 30 and opening 28 extend through the top layer 14, adhesive layer 20, and hydrogel material 22. Where the optional support layer 38 is included, the slit 30 and opening 28 also extend through support layer 38. The opening 28 is appropriately sized to receive a retaining pin 56 and to maintain a relatively tight seal between the retaining pin 56 and the dressing 12.

Figure 5:
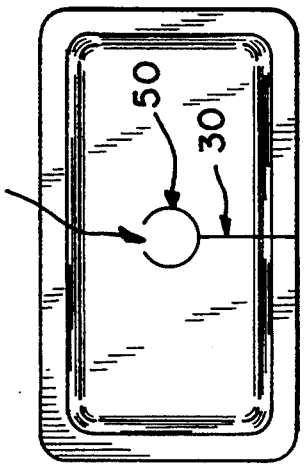
FIG. 5 is a top view of the external fixation dressing, illustrating an opening formed by a C-shaped cut.

In the embodiment shown in FIG. 5, the opening 28 results from the hinged portion 52 being displaced away from the skin of the patent. When the dressing 12 is applied around a retaining pin 56, the cut portion will be moved away from the patient's skin, but will remain attached to the dressing 12. The opening 52 is sized to be just slightly smaller in diameter than the diameter of the external fixation pin with which the dressing is to be used. By this arrangement, a good seal around the pin is provided.

It will be appreciated that the asterisk-shaped cuts 54 in the embodiment shown in FIG. 6 result in a dressing having the ability to accommodate a wider range of external fixation pin sizes. The pin will extend through the dressing at the intersection of the cuts 54. The V-shaped portions of the dressing between adjacent cuts will be folded away from the skin of the patient by an amount that is sufficient to permit the pin to be received in the resulting opening.

Having described the invention in detail and by reference to the preferred embodiments thereof, it will be apparent that modifications and variations are possible without departing from the scope of the invention which is defined in the appended claims.

What is claimed is:

1. An external fixation dressing for bandaging the area around an external fixation retaining pin, comprising:
    a thin-film top layer having a first side and a second side;
    an adhesive layer positioned on said second side of said top
    a hydrogel layer having a first side and a second side, said first side of side hydrogel layer being positioned on said adhesive layer such that said adhesive layer resides between said top layer and said hydrogel layer, said dressing defining a substantially centered opening which extends through said top layer, said adhesive layer, and said hydrogel layer, wherein said opening is defined by a C-shaped cut having a hinged portion, the diameter of said opening being sized to receive a retaining pin.

2. An external fixation dressing as claimed in claim 1, wherein said top layer, said adhesive layer, and said hydrogel layer transparent.

3. An external fixation dressing as claimed in claim 1, said dressing further defining a slit which extends from an outer edge of said dressing and intersects said openings, said slit extending through said top layer, said adhesive layer, and said hydrogel layer.

4. An external fixation dressing as claimed in claim 1, further comprising a release liner secured to said second side of said hydrogel layer.

5. An external fixation dressing as claimed in claim 1, further comprising a support layer having a first side and a second side and comprising a permeable fabric having a plurality of interstices therewith, said support layer secured to said first side of said hydrogel layer and located between said hydrogel layer and said adhesive layer, wherein said hydrogel layer penetrates said interstices to said first side of said support layer such that said hydrogel layer resides on both said first side and said second side of said support layer, said hydrogel layer being adhered to said second side of said top layer by means of said adhesive layer such that said first side of said support layer is adjacent to said second side of said top layer.

6. An external fixation dressing as claimed in claim 1, further comprising a porous backing layer having a first side and a second side; said first side of said backing layer being adhered to said second side of said top layer by means of said adhesive layer; said second side of said backing layer being adhered to said first side of said hydrogel layer; said dressing defining a substantially centered opening which extends through said hydrogel layer, said backing layer, said adhesive layer, and said top layer.

7. An external fixation dressing as claimed in claim 6, wherein said backing layer is formed of a porous material having sufficient porosity such that said second side of said backing layer is securable to said first side of said hydrogel layer.

8. An external fixation dressing as claimed in claim 6, wherein said backing layer comprises a filled polyolefin foam.

9. An external fixation dressing as claimed in claim 1, wherein said hydrogel layer comprises:
    (a) from about 0% to about 90% by weight polyhydric alcohol;
    (b) from about 6% to about 60% by weight aliphatic diisocyanate-terminated prepolymer;
    (c) from about 4% to about 40% by weight polyethylene oxide-based polyamine;
    (d) up to about 2% by weight sodium chloride; and
    (e) the balance water.

10. An external fixation dressing as claimed in claim 1, wherein said hydrogel layer comprises:
    (a) from about 15% to about 30% by weight polyhydric alcohol;
    (b) from about 8% to about 14% by weight isophorone diisocyanate-terminated prepolymer;
    (c) from about 5% to about 10% by weight polyethylene oxide-based diamine;
    (d) up to about 1% by weight sodium chloride; and
    (e) the balance water.

11. An external fixation dressing as claimed in claim 1, wherein said hydrogel layer comprises:
    (a) about 17% by weight polypropylene glycol;
    (b) about 12% by weight isophorone diisocyanate-terminated prepolymer;
    (c) about 9% by weight polyethylene oxide-based diamine;
    (d) about 1% by weight sodium chloride; and
    (e) about 61% by weight water.

12. An external fixation dressing for bandaging the area around an external fixation retaining pin, comprising:
    a thin-film top layer having a first side and a second side and defining a perimeter portion and a center portion;
    a first adhesive layer positioned on said second side of said top layer;
    a backing layer having a first side and a second side, said first side of backing layer being adhered to said second side of the top layer by means of said first adhesive layer;
    a hydrogel layer having a first side and a second side, said first side of said hydrogel layer being positioned on said second side of said backing layer; and
    a support layer having a first side and a second side and comprising a permeable fabric having a plurality of interstices therewithin; said support layer secured to said first side of said hydrogel layer and located between said hydrogel layer and said backing layer; wherein said hydrogel layer penetrates said interstices to said first side of said support layer such that said hydrogel layer resides on both said first side and said second side of said support layer;

said support layer being adjacent to said second side of said backing layer; said dressing defining a substantially centered opening and a slit which extends from an outer edge of said dressing intersects said opening; said opening and said slit extending through said top layer, said first adhesive layer, said backing layer, said support layer, and said hydrogel layer, said opening being defined by a C-shaped cut having a hinged portion; said top layer, said backing layer, said support layer, and said hydrogel layer being appropriately sized such that said top layer, said backing layer, said support layer, and said hydrogel layer reside entirely within said center portion of said second side of said top layer.

13. An external fixation dressing as claimed in claim 12, wherein said backing layer is formed of polyurethane, said dressing further comprising a second adhesive layer positioned on said second side of said backing layer, such that said first side of said hydrogel layer adheres to said second side of said backing layer by means of said second adhesive layer.

14. An external fixation dressing as claimed in claim 12, wherein said backing layer is formed of a porous material having sufficient porosity such that said second side of said backing layer is securable to said first side of said hydrogel layer.

15. An external fixation dressing as claimed in claim 12, further comprising a release liner positioned over said second side of said hydrogel material and secured to said perimeter portion of said second side of said top layer by means of said first adhesive layer.

16. An external fixation dressing for bandaging the area around an external fixation retaining pin, comprising:
   a thin-film top layer having a first side and a second side;
   an adhesive layer positioned on said second side of said top layer; and
   a hydrogel layer having a first side and a second side, said first side of said hydrogel layer being positioned on said adhesive layer such that said adhesive layer resides between said top layer and said hydrogel layer, said dressing defining a substantially centered opening which extends through said top layer, said adhesive layer, and said hydrogel layer, wherein said opening is defined by an asterisk-shaped plurality of intersecting cuts, the diameter of said opening being sized to receive a retaining pin.

17. An external fixation dressing as claimed in claim 16, wherein said top layer, said adhesive layer, and said hydrogel layer are transparent.

18. An external fixation dressing as claimed in claim 16, said dressing further defining a slit which extends from an outer edge of said dressing and intersects said opening, said slit extending through said top layer, said adhesive layer, and said hydrogel layer.

19. An external fixation dressing as claimed in claim 16, further comprising a release liner secured to said second side of said hydrogel layer.

20. An external fixation dressing as claimed in claim 16, further comprising a support layer having a first side and a second side and comprising a permeable fabric having a plurality of interstices therewith, said support layer secured to said first side of said hydrogel layer and located between said hydrogel layer and said adhesive layer, wherein said hydrogel layer penetrates said interstices to said first side of said support layer such that said hydrogel layer resides on both said first side and said second side of said support layer, said hydrogel layer being adhered to said second side of said top layer by means of said adhesive layer such that said first side of said support layer is adjacent to said second side of said top layer.

21. An external fixation dressing as claimed in claim 16, further comprising a porous backing layer having a first side and a second side; said first side of said backing layer being adhered to said second side of said top layer by means of said adhesive layer; said second side of said backing layer being adhered to said first side of said hydrogel layer; said dressing defining a substantially centered opening which extends through said hydrogel layer, said backing layer, said adhesive layer, and said top layer.

22. An external fixation dressing as claimed in claim 21, wherein said backing layer is formed of a porous material having sufficient porosity such that said second side of said backing layer is securable to said first side of said hydrogel layer.

23. An external fixation dressing as claimed in claim 21, wherein said backing layer comprises a filled polyolefin foam.

24. An external fixation dressing as claimed in claim 16, wherein said hydrogel layer comprises:
   (a) from about 0% to about 90% by weight polyhydric alcohol;
   (b) from about 6% to about 60% by weight aliphatic diisocyanate-terminated prepolymer;
   (c) from about 4% to about 40% by weight polyethylene oxide-based polyamine;
   (d) up to about 2% by weight sodium chloride; and
   (e) the balance water.

25. An external fixation dressing as claimed in claim 16, wherein said hydrogel layer comprises:
   (a) from about 15% to about 30% by weight polyhydric alcohol;
   (b) from about 8% to about 14% by weight isophorone diisocyanate-terminated prepolymer;
   (c) from about 5% to about 10% by weight polyethylene oxide-based diamine;
   (d) up to about 1% by weight sodium chloride; and
   (e) the balance water.

26. An external fixation dressing as claimed in claim 16, wherein said hydrogel layer comprises:
   (a) about 17% by weight polypropylene glycol;
   (b) about 12% by weight isophorone diisocyanate-terminated prepolymer;
   (c) about 9% by weight polyethylene oxide-based diamine;
   (d) about 1% by weight sodium chloride; and
   (e) about 61% by weight water.

27. An external fixation dressing for bandaging the area around an external fixation retaining pin, comprising:
   a thin-film top layer having a first side and a second side and defining a perimeter portion and a center portion;
   a first adhesive layer positioned on said second side of said top layer;
   a backing layer having a first side and a second side, said first side of said backing layer being adhered to said second side of the top layer by means of said first adhesive layer;
   a hydrogel layer having a first side and a second side, said first side of said hydrogel layer being positioned on said second side of said backing layer; and a support layer having a first side and a second side and comprising a permeable fabric having a plurality of interstices therewithin; said support layer secured to said first side of said hydrogel layer and located between said hydrogel layer and said backing layer; wherein said hydrogel layer penetrates said interstices to said first side of said support layer such that said hydrogel layer resides on both said first side and said second side of said support layer; said support layer being adjacent to said second side of said backing layer; said dressing defining a substantially centered opening and a slit which extends from an outer edge of said dressing intersects said opening; said opening and said slit extending through said top layer, said first adhesive layer, said backing layer, said support layer, and said hydrogel layer, said opening being defined by an asterisk-shaped plurality of intersecting cuts; said top layer, said backing layer, said support layer, and said hydrogel layer being appropriately sized such that said top layer, said backing layer, said support layer, and said hydrogel layer reside entirely within said center portion of said second side of said top layer.

28. An external fixation dressing as claimed in claim 27, wherein said backing layer is formed of polyurethane, said dressing further comprising a second adhesive layer positioned on said second side of said backing layer, such that said first side of said hydrogel layer adheres to said second side of said backing layer by means of said second adhesive layer.

29. An external fixation dressing as claimed in claim 27, wherein said backing layer is formed of a porous material having sufficient porosity such that said second side of said backing layer is securable to said first side of said hydrogel layer.

30. An external fixation dressing as claimed in claim 27, further comprising a release liner positioned over said second side of said hydrogel material and secured to said perimeter portion of said second side of said top layer by means of said first adhesive layer.

* * * * *